United States Patent [19]

Notsu et al.

[11] Patent Number: 5,306,404
[45] Date of Patent: Apr. 26, 1994

[54] PROCESS FOR PREPARING POLYACRYLAMIDE GEL PLATE FOR ELECTROPHORESIS

[75] Inventors: Kazuaki Notsu, Abiko; Nobuyoshi Ebata, Takizawa; Akiko Udagawa, Tokyo; Mieko Shiratori, Abiko, all of Japan

[73] Assignee: Daiichi Pure Chemicals Co., Ltd., Tokyo, Japan

[21] Appl. No.: 9,109

[22] Filed: Jan. 26, 1993

[30] Foreign Application Priority Data

Jan. 28, 1992 [JP] Japan ................... 4-013174

[51] Int. Cl.$^5$ ............................... C25B 7/00
[52] U.S. Cl. ................. 204/182.8; 252/315.1; 356/344
[58] Field of Search ............... 204/182.8; 256/344; 252/315.1

[56] References Cited

U.S. PATENT DOCUMENTS 4,834,853  5/1989  Sugihara et al. .............. 204/182.8
4,891,119  1/1990  Ogawa ........................ 204/182.8

FOREIGN PATENT DOCUMENTS 0139471   5/1985  European Pat. Off. ......... 204/182.8
63-313050 12/1988  Japan .
63-313052 12/1988  Japan .
63-313054 12/1988  Japan .

*Primary Examiner*—John Niebling
*Assistant Examiner*—Cybille Delacroix-Muirheid
*Attorney, Agent, or Firm*—Bacon & Thomas

[57] ABSTRACT

A process for preparing a polyacrylamide gel plate for electrophoresis with any desired concentrations, which comprises mixing a high concentration acrylamide monomer solution, a low concentration peroxide solution, and a low concentration reducing solution at an arbitrary ratio, and introducing the mixture into a gel supporter. The process enables preparation of a large quantity of high quality polyacrylamide gel plates for electrophoresis which is useful for analysis of high molecular weight in vivo components typified by proteins with a good reproducibility. It also contributes to the production of various gels having a plurality of gel concentrations or having a specified concentration gradient, and serves for improving the productivity of multi-products manufacturing of such gel plates.

11 Claims, 5 Drawing Sheets

A: Peroxide solution
B: Reducing agent solution
C: Monomer solution

A: Peroxide solution
B: Reducing agent solution
C: Monomer solution

PROCESS FOR PREPARING POLYACRYLAMIDE GEL PLATE FOR ELECTROPHORESIS

BACKGROUND OF THE INVENTION

1. Field of the Invention

The present invention relates to a process for preparing a polyacrylamide gel plate for use in electrophoresis, and, more particularly, to a process for preparing a large quantity of polyacrylamide gel plates which are especially suitable for electrophoresis analysis of in vivo components with a high molecular weight, such as proteins and the like.

2. Description of the Background Art

Polyacrylamide gels have widely been used for electrophoresis analysis of in vivo components with a high molecular weight, e.g., protein, nucleic acid, and the like. Usually, these polyacrylamide gels are prepared by cross-linking polymerization of a monomer and a cross-linking agent; i.e., by adding a polymerization initiator to a 2-40% by weight aqueous solution comprising a monomer such as acrylamides and a divalent or polyvalent cross-linking agent such as N,N'-methylenebisacrylamide (such a solution is hereinafter sometimes referred to as an "acrylamide monomer solution").

As an initiation method of polymerization, either a combination of a peroxide and a reducing agent, or a combination of a peroxide, a reducing agent, a photosensitation agent and exciting ray, while the reducing agent is not necessarily used, may be used. For the latter photopolymerization method, although some methods are proposed, in which the polymerization does not take place before the light irradiation, even after a polymerization initiator added (e.g., Japanese Patent Laid-open (kokai) No. 91849/1987), the photopolymerization method basically involves many technical problems for obtaining stable gel products with a good reproducibility. The problems are found in difficulties in controlling the polymerization reaction such as shading of the reaction liquid for gel formation, selection of irradiation conditions for producing gel, and occurrence of continued polymerization in the presence of light even after the completion of gel formation. For these reasons, the former chemical polymerization method, which adopts a combination of a peroxide and a reducing agent, is preferred owing to its comparatively easy handling of the reaction liquid and capability of controlling the reaction to some extent by adjusting the amount of the catalyst used.

In the chemical polymerization method, however, since the gel reaction takes place immediately after the addition of the polymerization initiator to the monomer solution, giving rise to a viscosity increase of the solution and to gelatinization of the mixture, it is necessary to prepare a monomer solution and a polymerization initiator solution separately and mix them just before the start of the gel forming process. This separate addition of a peroxide solution and a reducing solution to the monomer solution inevitably requires complicated steps. On the other hand, if these two solutions are mixed together beforehand, the catalyst activity will change as the time passes, making it difficult to stably obtain high quality gels.

Furthermore, since a molecular sieve effect of a polyacrylamide gel varies depending on the gel concentrations, various products with different gel concentrations are required conforming to molecular weights or the like of the components to be separated or analyzed. Conventionally, this requirement for polyacrylamide gels has been fulfilled by preparing a monomer solution having a specific gel concentration, which corresponds to the subject to be separated for analysis, then adding a polymerization initiator to the solution and introducing the mixture into or spreading it over a gel-supporter. This necessitates to prepare many gel-forming solutions with different concentrations when the subjects to be analyzed contain a number of components. In addition, preparation of a gel with a concentration gradient suitable for the analysis of a subject comprising a wide molecular weight distribution is implemented by providing two monomer solutions with different concentrations, one a low concentration and the other a high concentration, and adding a polymerization initiator to the solutions. The solutions are then introduced into or spread over a gel-supporter by using a gradient forming unit. In order to obtain a number of gels with different concentration gradients, it is necessary, in the same manner as in the preparation of a series of gels with a specified concentration, to prepare beforehand various monomer solutions with different concentrations corresponding to the required gradients, and to appropriately combine these solutions. Furthermore, in order to prepare a stable gel, the amount of the polymerization initiator must be adjusted appropriately so that not too less or not too much of it is incorporated relative to the concentration of the monomer solution to be used.

As noted above, stable supply of high quality polyacrylamide gels in large quantities has been difficult to achieve by conventional preparation methods which involve rather complicated manufacturing steps and require sophisticated skills.

An object of the present invention is, therefore, to provide an easy production process which can prepare a large quantity of various kinds of high quality and stable acqueous polyacrylamide gels, having a high resolving power and any desired concentrations or concentration gradients, with a good reproducibility, and which does not involve the problem of changes in the polymerization initiator activity before being introduced into a gel-supporter or does not require to prepare many monomer solutions or many polymerization initiator solutions of different concentrations beforehand.

In view of this situation, the present inventors have undertaken intensive studies to solve the aforementioned problems, and found that a high quality gel with a desired concentration can constantly and easily be prepared with a good reproducibility and without any changes in the catalyst activity using an optimum amount of a polymerization initiator, by simply preparing one monomer solution with a high concentration, one peroxide solution with a low concentration, and one reducing solution with a low concentration, and mixing them at an appropriate ratio prior to use. These findings have led to the completion of the present invention.

SUMMARY OF THE INVENTION

Accordingly, an object of this invention is to provide a process for preparing a polyacrylamide gel plate for electrophoresis with a desired concentration which comprises mixing an acrylamide monomer solution with a high concentration, a peroxide solution with a low concentration, and a reducing agent solution with a low concentration, at an arbitrary ratio, and introducing the mixture into a gel-supporter.

In a preferred embodiment, the concentration of said acrylamide monomer solution is in the range of 20–50% by weight, and the concentrations of said peroxide solution and reducing agent solution are respectively 0.005–1.0% by weight; and said arbitrary concentration is in the range of 2–50 w/v %.

Another object of the present invention is to provide a process for preparing said polyacrylamide gel plate for electrophoresis in which the mixing of said acrylamide monomer solution, peroxide solution, and reducing agent solution are implemented simultaneously, using or not using a computer control system.

Still another object of the present invention is to provide a process for preparing said polyacrylamide gel plate for electrophoresis in which said polyacrylamide gel has a plurality of concentrations or a concentration gradient.

Other objects, features and advantages of the invention will hereinafter become more readily apparent from the following description.

DETAILED DESCRIPTION OF THE INVENTION AND PREFERRED EMBODIMENTS

Figure 1:
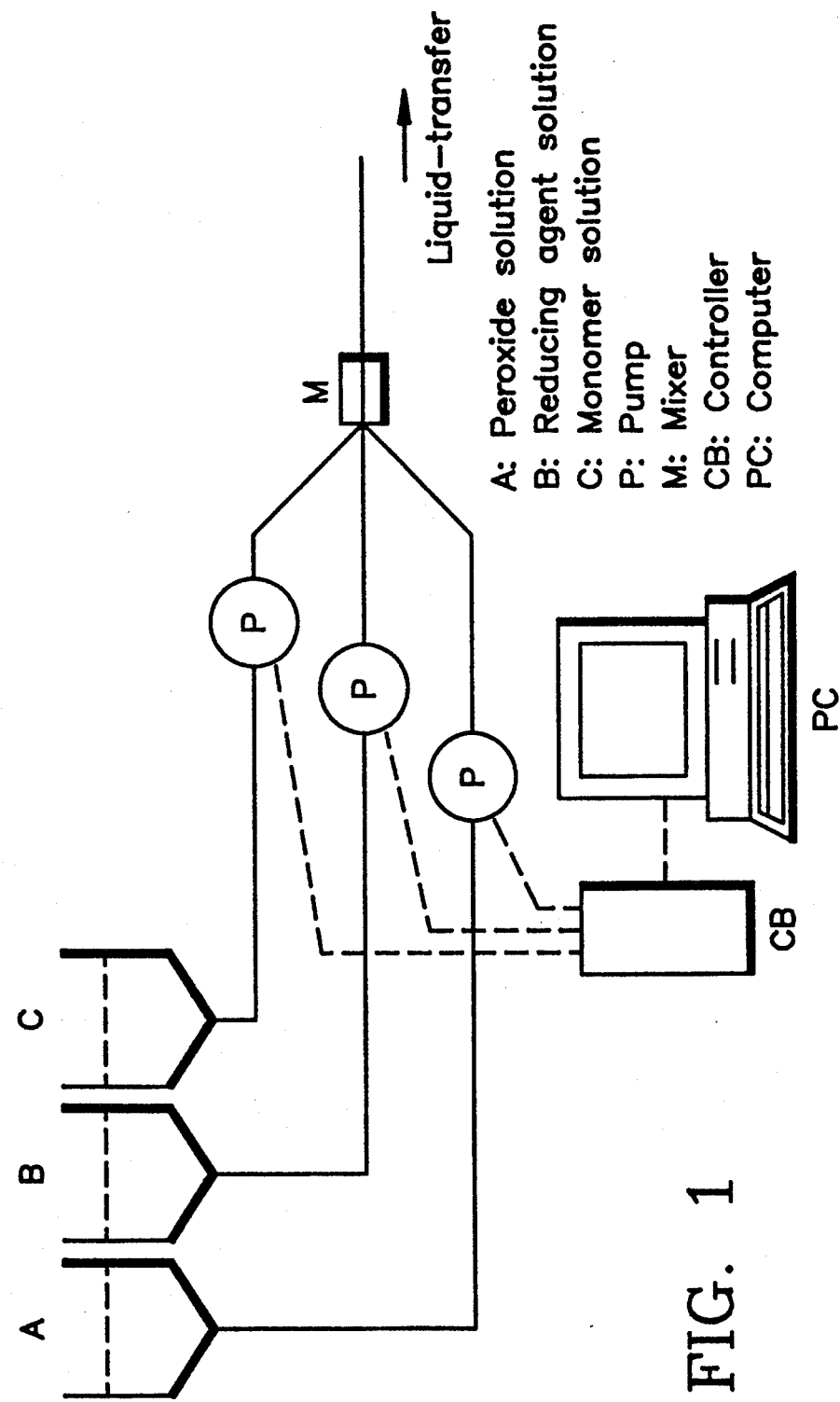
FIG. 1 shows the outline of a preferred embodiment of the process of the present invention.

In the practice of the present invention, the solutions to be prepared beforehand are only three kinds; one acrylamide monomer solution with a high concentration, one peroxide solution with a low concentration, and one reducing agent solution with a low concentration. There is no need to prepare many kinds of monomer solutions beforehand. It is possible to prepare a large amount of these solutions at a time and use it either continually or recurrently whenever required by taking out a small amount of these solutions.

The high concentration acrylamide monomer solution used in the present invention contains an acrylamide monomer and a cross-linking agent, and as required, an anionic surface active agent as a modifier, a pH buffering agent, and the like.

Examples of acrylamide monomers include acrylamide homologues such as acrylamide, N-methylacrylamide, N,N'-dimethylacrylamide, N-(hydroxymethyl)acrylamide, diacetoneacrylamide, and the like; methacrylamide; and the like. These compounds can be used individually or in combination of two or more. Among these compounds, acrylamide is preferred, and the combined use of acrylamide with one or more of other acrylamide monomers is also possible.

As a cross-linking agent, any compounds which possess divalent, trivalent or more cross-linking function can be used. Specific examples of the divalent compounds are N,N'-methylenebisacrylamide (BIS), N,N'-propylenebisacrylamide, diacrylamide dimethyl ether, piperazine diacrylamide, and the like. Of these cross-linking agents, BIS is preferred. One or more of these cross-linking agents can be used together in combination.

As an anionic surface active agent, alkyl sulfates, particularly those containing a long chain alkyl group with more than 10 carbon atoms are preferable. The most preferred is sodium dodecyl sulfate (SDS).

Various types of pH buffering agents can be found by reference to "Chemistry Handbook—Fundamental Part" (edited by The Chemical Society of Japan) and the like. Enumerated as specific examples are Tris(hydroxymethyl)aminomethane (Tris), N,N'-bis(2-hydroxyethyl)glycine, sodium N-2-hydroxypiperazine-N'-2-hydroxypropane-3-sulfonate, as well as any acids, alkalis, or salts used, as required, in combination with one of these compounds. Tris-hydrochloride buffer (pH 7.0–9.2) is an example of such a buffering agent which is most popularly used.

The concentration of the acrylamide monomer solution, in terms of the sum of acrylamide monomers and cross-linking agents contained, used in the present invention is preferably higher than the concentration usually required, for example, 10–98% by weight, and more preferably 20–50% by weight. The amount of the cross-linking agent is preferably in the range of 1–30% by weight, with the particularly preferable range being 2–10% by weight, based on the total amount of the monomer and the cross-linking agent.

Preparation of the acrylamide monomer solution may be implemented by dissolving or dispersing the aforementioned components into water or a mixed solution of water and an organic solvent.

The peroxide compound to be used in the present invention may be any peroxides disclosed in known references on electrophoresis ("Electrophoresis—Fundamentals and Experiments", edited by H. Terada, and the like.) and includes ammonium peroxodisulfate, an alkali metal peroxodisulfate, and the like.

The concentration of the peroxide solution must be low, for example, 0.001–5.0% by weight, or more preferably 0.005–1.0% by weight, from the aspect of its functions as a diluent for the monomer solution and as a polymerization initiator. Preparation of the peroxide solution may be implemented by dissolving or dispersing said peroxide and, as required, anionic surface active agents, pH buffering agents, and the like into water or a mixed solution of water and an organic solvent.

The reducing agents to be used in the present invention may be amine compounds disclosed in known references on electrophoresis ("Electrophoresis—Fundamentals and Experiments", edited by H. Terada, and the like.). Specific examples include N,N,N',N'-tetramethylethylenediamine (TEMED), N,N,-dimethylethylenediamine, 3-dimethylamino-n-propylamine, 3-dimethylaminopropionitrile, N-n-butyldimethylamine, N,N'-dimethylpiperazine, and the like.

The concentration of the reducing agent solution must be low, for example, 0.001–5.0% by weight, and more preferably 0.005–1.0% by weight, from the aspect of its functions as a diluent for the monomer solution and as a polymerization initiator. Preparation of the reducing agent solution may be implemented by dissolving or dispersing said reducing agent and, as required, anionic surface active agents, pH buffering agents, and the like into water or a mixed solution of water and an organic solvent.

When preparing a mixed solution of any desired gel concentration by mixing these three solutions, namely a high concentration acrylamide monomer solution, a low concentration peroxide solution, and a low concentration reducing solution, which have been separately prepared beforehand, it is desirable to mix and stir these three solutions at a time in order to avoid the occurrence of reactions between peroxides and reducing agents. The term "any desired gel concentration" herein means that the concentration of the acrylamide monomer and the crosslinking agent contained in the gel can arbitrarily be controlled. Usually, the gel concentration is adjusted in the range of 2–50 w/v %. The introduction of the mixed solution to a gel-supporter can be performed by transferring the solution or spreading it over the gel-supporter. As the gel-supporter, any known support material which is conventionally used, such as a glass tube, a glass plate, an organic polymer, or the like, can be employed.

Figure 2:
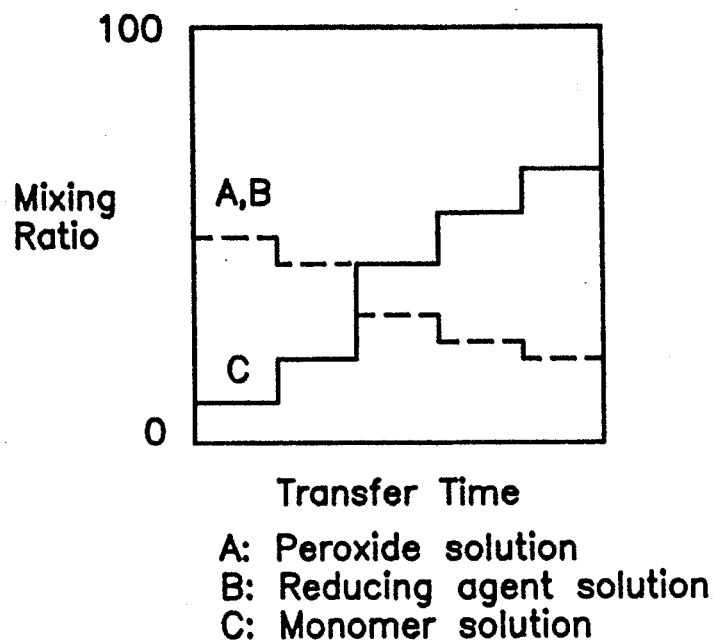
FIG. 2 shows an example of a mixing pattern of the three solutions of the present invention; peroxide solution (A), reducing agent solution (B), and high concentration monomer solution (C), wherein the concentrations are changed stepwise.
Figure 3:
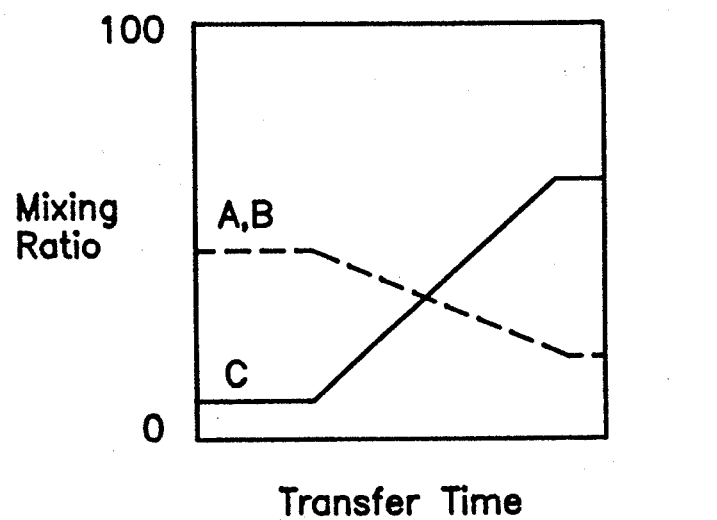
FIG. 3 shows an example of a mixing pattern of the three solutions of the present invention; peroxide solution (A), reducing agent solution (B), and high concentration monomer solution (C), wherein the concentrations are continuously changed.

A preferable example of the process of mixing these three solutions and introducing it into the gel-supporter is presented in FIG. 1. The three solutions, peroxide solution (A), reducing agent solution (B), and monomer solution (C), are transferred respectively by pumps (P) and stirred and mixed by a mixer (M) and introduced into the gel-supporter. In this process, any target solutions having a desired gel concentration can be prepared by adjusting the flow ratio of the pumps by which the three solutions are transferred. In addition, if the flow ratio of the pumps is designed to be controlled by a computer (PC) via a controller (CB), the gel concentrations of the solution can be changed stepwise as shown in FIG. 2, or it is possible to form a concentration gradient easily by changing the flow ratio continuously as shown in FIG. 3.

The electrophoresis gel plates prepared by this invention are desired to be substantially colorless and transparent for making it easy to detect and read the electrophoresis images.

The electrophoresis gel plates prepared by this invention can be applied to horizontal or vertical electrophoresis, and the like, according to a known method disclosed in the aforementioned literature, patent applications, and the like.

Other features of the invention will become apparent in the course of the following description of the exemplary embodiments which are given for illustration of the invention and are not intended to be limiting thereof.

EXAMPLES

Example 1

Gel-forming Solutions A (A1–A3) of the present invention and Comparative Solutions B, consisting of Solution (B1) which is a mixture of a peroxide and a reducing agent and Solution (B2) which is a mixture of acrylamide and a cross-linking agent, were prepared using the formulations given in Table 1. These solutions were degassed to adjust the content of dissolved oxygen and stored at 4° C. under a helium atmosphere. After certain periods of time specified in Table 2, each solution was taken out and mixed together at 4° C. with a specified ratio to obtain solutions of the same gel-content. After mixing, the time required for each solution to begin to gelatinize, i.e, the period of time required for the temperature of the solution to begin to rise by the exothermic reaction (hereinafter referred to as "Gelatinized Time"), was measured and determined as given in Table 2.

The Gelatinized Time for Solution A showed a constant value irrespective of the time elapsed, whereas that for Solutions B varied depending on the elapsed periods, and ultimately, Solution B showed no gelatinization after 24 hours, even though Solutions B1 and B2 were mixed. In addition, when slab-type electrophoresis gel plates were prepared from Solution A and Solution B, which had been prepared and stored under the same conditions, the gel plates prepared from Solution A did not show any effects due to the elapsed time, while the gel plates from Solution B gave a stringy appearance as a whole as the time elapsed, producing strains on phoresis images.

TABLE 1

| Components for Gel Forming Solution | Invention Composition A | | | Comparative Composition B | |
| --- | --- | --- | --- | --- | --- |
| | Peroxide Solution (A1) | Reducing Agent Solution (A2) | Monomer Solution (A3) | B1 | B2 |
| Acrylamide | — | — | 390 g | — | 390 g |
| BIS | — | — | 10 g | — | 10 g |
| pH buffering agent | 250 ml | 250 ml | 250 ml | 250 ml | 250 ml |
| APS | 0.07 g | — | — | 0.035 g | — |
| TEMED | — | 0.06 ml | 0.03 ml | 0.03 ml | 0.03 ml |
| Water (an amount making the total volume 1000 ml) | Balance | Balance | Balance | Balance | Balance |

Note:
BIS: N,N'-methylenebisacrylamide (Cross-linking agent)
pH buffer: 1.5M Tris(hydroxymethyl)aminomethane-hydrocholide, pH 8.8
APS: Ammoniumperoxodisulfate (Peroxide)
TEMED: N,N,N',N'-tetramethylethylenediamine (Reducing agent)

TABLE 2

| Gelatinized Time (minutes) | Elapsed Time (hours) | | | | | |
|---|---|---|---|---|---|---|
| | 0 | 1 | 4 | 8 | 12 | 24 |
| Solution A | 35 | 34 | 35 | 33 | 34 | 35 |
| Solution B | 35 | 30 | 30 | 45 | 80 | —* |

Note: "Solution A" was formulated with a mixing ratio of A1:A2:A3 = 3:3:2, while "Solution B" was formulated with a mixing ratio of B1:B2 = 3:1, at every elapsed time, to prepare gel-forming solutions containing 10% acrylamide.
*Solution B was not gelatinized at 24 hours or later.

As illustrated above, the process of this invention can avoid changes in the catalyst activity due to interactions between a peroxide and a reducing agent so that the target gels can always be produced under consistent polymerization conditions, with a good reproducibility. Furthermore, the solutions once prepared can be used continually or kept stored over a long period of time.

Example 2

Figure 4:
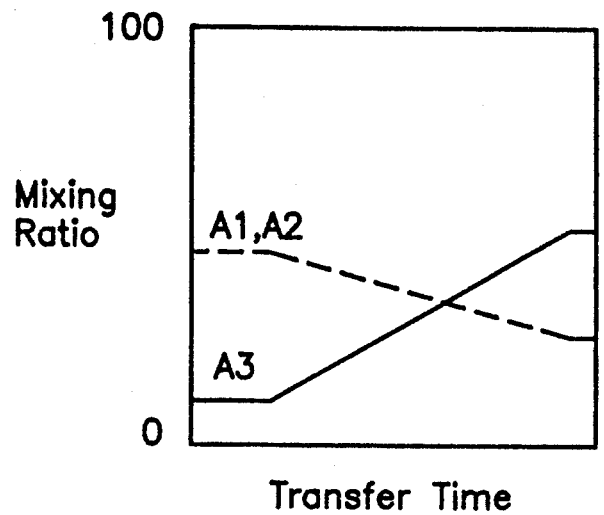
FIG. 4 shows a liquid-transfer pattern of peroxide solution (A1), reducing agent solution (A2), and high concentration monomer solution (A3) employed in Example 2.
Figure 5:
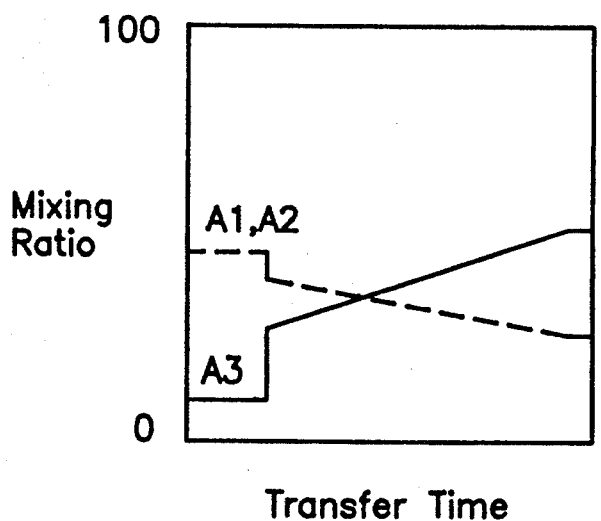
FIG. 5 shows a liquid-transfer pattern of peroxide solution (A1), reducing solution (A2), and high concentration monomer solution (A3) employed in Example 2.
Figure 6:
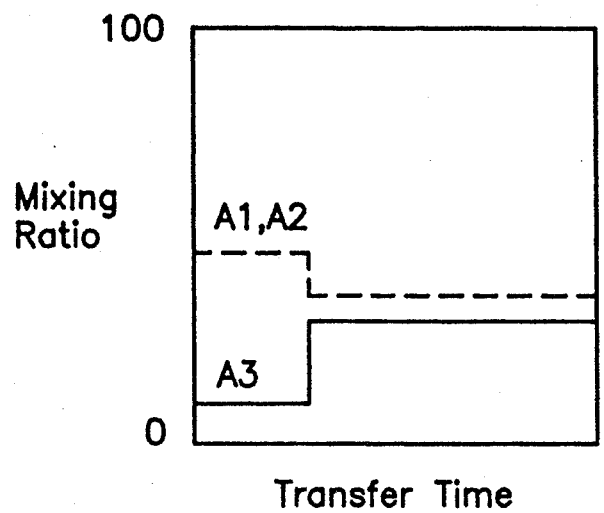
FIG. 6 shows a liquid-transfer pattern of peroxide solution (A1), reducing agent solution (A2), and high concentration monomer solution (A3) employed in Example 2.
Figure 7:
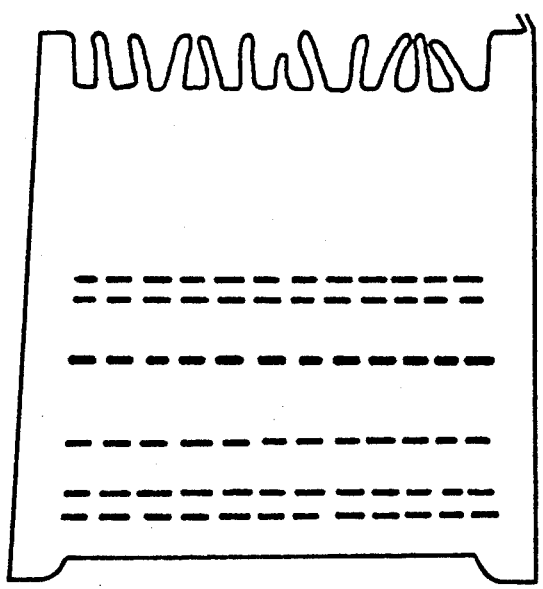
FIG. 7 shows an electrophoresis image of the gel plate obtained by the liquid-transfer according to the pattern indicated in FIG. 4.
Figure 8:
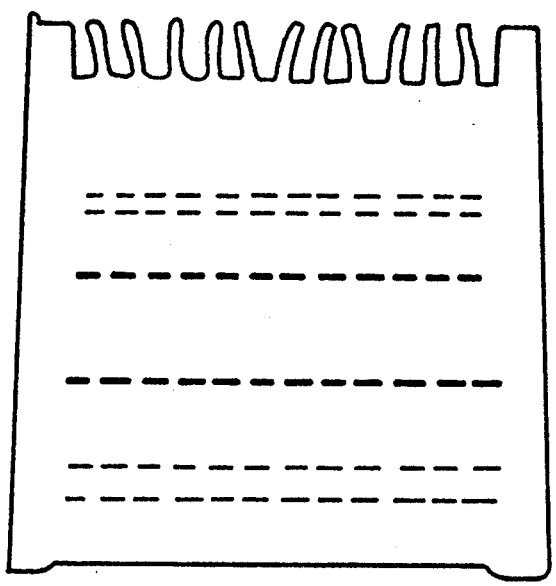
FIG. 8 shows an electrophoresis image of the gel plate obtained by the liquid-transfer pattern indicated in FIG. 5.
Figure 9:
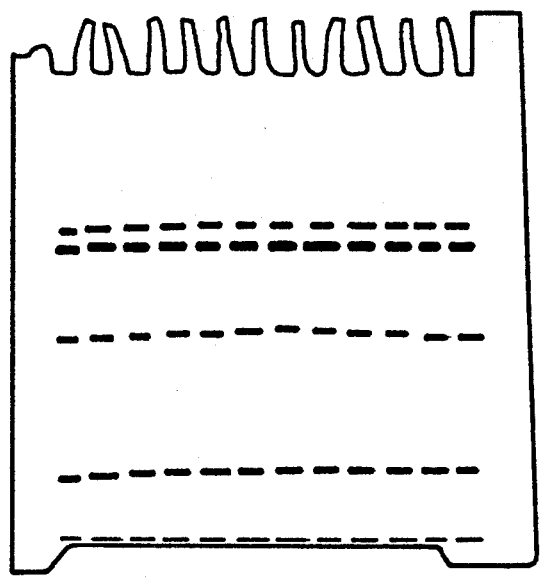
FIG. 9 shows an electrophoresis image of the gel plate obtained by the liquid-transfer according to the pattern indicated in FIG. 6.

Gel-forming Solutions A (A1-A3) of the present invention were prepared according to the formulations given in Table 1, and the solutions were served for producing slab-type electrophoresis gel plates using an equipment shown in FIG. 1 by changing the flow ratio as shown in FIGS. 4-6. The gel plates thus prepared were subjected to SDS-polyacrylamide gel electrophoresis according to a known reference on electrophoresis using a mixture of proteins whose molecular weights were known, as a molecular-weight marker. The electrophoresis images obtained in this test are presented in FIGS. 7-9. According to the process of this invention, any gels with a desired gel concentration or a desired concentration gradient can be produced by simply changing the mixing pattern of three solutions. This versatility is quite advantageous for preparing many kinds of products without complicated procedure changes.

High quality polyacrylamide gel plates for electrophoresis, which are useful for analysis of high molecular weight in vivo components typified by proteins, can be prepared in large quantities with a good reproducibility by the process of this invention. This is not only advantageous for the production of various gels with different gel concentrations or different concentration gradients, but also serves for improving the productivity of multi-products manufacturing.

Obviously, numerous modifications and variations of the present invention are possible in light of the above teachings. It is therefore to be understood that within the scope of the appended claims, the invention may be practiced other than as specifically described herein.

What is claimed is:

1. A process for preparing a polyacrylamide gel plate for electrophoresis having a concentration of 2-50 w/v % and having a plurality of concentrations or a concentration gradient, comprising the steps of simultaneously mixing the following:
   (a) an acrylamide monomer solution, which comprises an acrylamide monomer and a cross-linking agent, the acrylamide monomer solution being in the range of 20-50% by weight;
   (b) a peroxide solution having a concentration of 0.005-1.0% by weight; and
   (c) a reducing agent solution having a concentration of 0.005-1.0% by weight; and introducing the mixture into a gel supporter.

2. A process according to claim 1, wherein said mixing of the acrylamide monomer solution, peroxide solution, and reducing agent solution is implemented simultaneously by a computer control system.

3. A process according to claim 1, wherein the acrylamide monomer is one or more acrylamide homologues selected from the group consisting of: acrylamide; N-methylacrylamide; N,N'-dimethylacrylamide; N-(hydroxymethyl)acrylamide; diacetoneacrylamide; and methyacrylamide.

4. A process according to claim 1, wherein the cross-linking agent is one or more selected from the group consisting of: N,N'-methylene bisacrylamide; N,N'-propylenebisacrylamide; diacrylamide dimethyl ether; piperazine; and diacrylamide.

5. A process according to claim 1, wherein the peroxide solution is comprised of a peroxide selected from the group consisting of: ammonium peroxidisulfate or an alkali metal peroxodisulfate.

6. A process according to claim 1, wherein the reducing agent solution comprises a reducing agent selected from the group consisting of: N,N,N', N'-tetramethylethylenediamine; N,N'-dimethylethylenediamine; 3-dimethylamino-n-propylamine; 3-dimethylaminopropionitrile; N-n-butyldimethylamine; and N,N'-dimethylpiperazine.

7. A process according to claim 1, wherein the acrylamide monomer solution further comprises one or both of an anionic surface active agent and a pH buffering agent.

8. A process according to claim 1, wherein the peroxide solution further comprises one or both of an anionic surface active agent and a pH buffering agent.

9. A process according to claim 1, wherein the reducing agent further comprises one or both of an anionic surface active agent and a pH buffering agent.

10. A process according to claim 1, wherein the cross-linking agent is in the range of 1-30% by weight based on the total amount of a monomer and cross-linking agent.

11. A process according to claim 1, wherein the cross-linking agent is in the range of 2-10% by weight based on the total amount of monomer and cross-linking agent.

* * * * *